United States Patent [19]

Itoh et al.

[11] Patent Number: 5,041,587
[45] Date of Patent: Aug. 20, 1991

[54] PROCESS FOR PREPARING ORGANIC SILICON COMPOUND

[75] Inventors: Masayoshi Itoh; Kenji Iwata, both of Yokohama; Noriyuki Yanagawa, Hatano; Tetsura Utsumi, Hiratsuka; Mineo Kobayashi, Yokohama; Ryo Takeuchi; Tomohiro Abe, both of Yokosuka, all of Japan

[73] Assignee: Mitsui Toatsu Chemicals, Inc., Tokyo, Japan

[21] Appl. No.: 478,366

[22] Filed: Feb. 12, 1990

[30] Foreign Application Priority Data

Feb. 14, 1989 [JP] Japan .................................. 1-32641

[51] Int. Cl.$^5$ .......................... C07F 7/10; C07F 7/08; C07F 7/18
[52] U.S. Cl. ........................... 556/413; 556/430; 556/431; 556/435; 556/436; 556/438; 556/440; 556/468; 556/481; 556/487
[58] Field of Search .............. 556/413, 430, 431, 435, 556/436, 438, 440, 487, 481, 468

[56] References Cited

U.S. PATENT DOCUMENTS

| | | | |
|---|---|---|---|
| 2,379,821 | 7/1948 | Miller et al. | 556/481 X |
| 2,469,355 | 5/1949 | De Pree et al. | 556/481 |
| 2,511,820 | 6/1950 | Barry et al. | 556/481 X |
| 2,546,330 | 3/1951 | Barry et al. | 556/481 |
| 2,682,512 | 6/1952 | Agre | 556/481 X |
| 2,770,634 | 11/1956 | Weyenberg | 556/481 |
| 3,560,541 | 2/1971 | Graf et al. | 556/481 |
| 3,666,782 | 5/1972 | Mui et al. | 556/481 |
| 3,706,776 | 12/1972 | Seiler et al. | 556/481 |

OTHER PUBLICATIONS

Gmelin Handbook of Inorganic Chemistry, 8th Edition, pp. 122, 140 and 192.

Primary Examiner—Paul F. Shaver
Attorney, Agent, or Firm—Burns, Doane, Swecker & Mathis

[57] ABSTRACT

A process for preparing an organic silicon compound is here disclosed which comprises the step of reacting a halogenated hydrocarbon selected from the group consisting

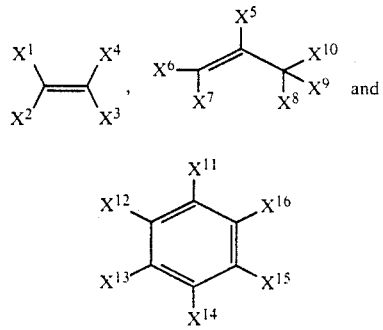

wherein each of $X^1$ to $X^{16}$ is selected from the group consisting of hydrogen, an alkyl group, alkenyl group, phenyl group, naphthyl group, alkoxy group, acyl group, alkylamino group and dialkylamino group having 1 to 20 carbon atoms which are unsubstituted or substituted and a halogen atom; and each of at least one of $X^1$ to $X^4$, at least one of $X^8$ to $X^{10}$ and at least one of $X^{11}$ to $X^{16}$ is a halogen atom, with a silane selected from the group consisting of $SiH_4$, $Si_2H_6$ and $Si_3H_8$.

9 Claims, No Drawings

PROCESS FOR PREPARING ORGANIC SILICON COMPOUND

BACKGROUND OF THE INVENTION

1. Field of the Invention

The present invention relates to a process for preparing an organic silicon compound.

2. Description of the Prior Art

Usually, "an organic silicon compound" is a general term for compounds each having an Si-C bond. In recent years, the chemical industry regarding the organic silicon compounds has been making amazing strides, as typified by silicones (polyorganosiloxanes). In most cases, the starting materials of the organic silicon compounds are alkylchlorosilanes obtained by Rochow's direct process, which can be exhibited by the following formula:

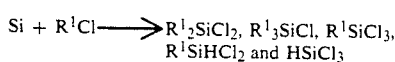

wherein $R^1$ is industrially limited to a methyl group or a phenyl group. Therefore, it is inevitable to rely on uneconomical methods such as the Grignard method in introducing a group other than the methyl group and phenyl group and an $LiAlH_4$ reduction method in synthesizing the alkylchlorosilane having an Si-H bond. That is, examples of conventional organic silicon compounds are substantially limited to compounds containing bonds of

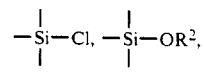

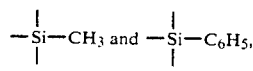

and thus except for $R^1SiHCl_2$ and $HSiCl_3$, compounds containing bond units of

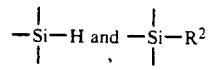

(wherein $R^2$ is an alkyl group or phenyl group other than the methyl group and phenyl group) which are concerned with the present invention have scarcely been utilized so far.

On the other hand, the current mass production of $SiH_4$, $Si_2H_6$ and $Si_3H_8$ (hereinafter referred to simply as "silanes") has become possible along with the development of the semiconductor industry, and so these silanes are inexpensively and easily available. In connection with techniques for manufacturing organic silicon compounds by the use of these kinds of silanes, research has scarcely been conducted, and a hydrosilyl formation reaction between an unsaturated hydrocarbon (having C=C or C≡C) and $SiH_4$ is only known [e.g., Z. Naturforsch, 56, 444 (1950); J. Am., Chem. Soc., 76, 3897 (1954); and PCT Application, International Laid-open Publication No. WO 88/05779]. With regard to reactions between $SiH_4$ and halogenated hydrocarbons concerning the present invention, a thermal reaction between $SiH_4$ and vinyl chloride has been reported in Z. Naturforsch, 76, 379-385 (1952), but the production of the organic silicon compounds (in this case, vinylsilane, divinylsilane and the like) which the present invention intends is not found at all in the above-mentioned report.

SUMMARY OF THE INVENTION

An object of the present invention is to provide a process for preparing an organic silicon compound economically which cannot be heretofore produced beneficially on an industrial scale.

Another object of the present invention is to provide a process for preparing an organic silicon compound by the use of a halogenated hydrocarbon and $SiH_4$, $Si_2H_6$ or $Si_3H_8$ which is a new basic raw material.

Additional objects and advantages of the present invention will be set forth in part in the description which follows, and in part will be obvious from the description, or may be learned by practice of the invention. The objects and advantages of the invention will be realized and attained by means of the instrumentalities and combinations, particularly pointed out in the appended claims.

The present invention have paid much attention to silanes as raw materials in the organic silicon industry, and they have intensively conducted research to develop an industrial route for the manufacture of the organic silicon compounds from these raw materials. As a result, the present invention has been completed.

To achieve the objects and in accordance with the purpose of the invention, as embodied and broadly described herein, the present invention comprises a process for preparing an organic silicon compound by reacting a halogenated hydrocarbon selected from the group consisting of

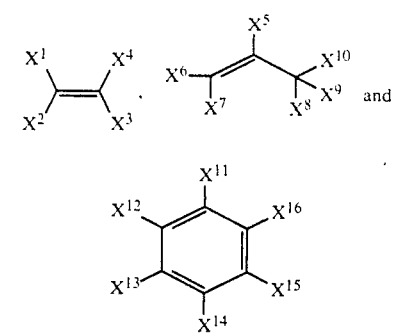

wherein each of $X^1$ to $X^{16}$ is selected from the group consisting of hydrogen, an alkyl group, alkenyl group, phenyl group, naphthyl group, alkoxy group, acyl group, alkylamino group and dialkylamino group having 1 to 20 carbon atoms which are unsubstituted or substituted and a halogen atom; and each of at least one of $X^1$ to $X^4$, at least one of $X^8$ to $X^{10}$ and at least one of $X^{11}$ to $X^{16}$ is a halogen atom, with a silane selected from the group consisting of $SiH_4$, $Si_2H_6$ and $Si_3H_8$.

According to the present invention, the organic silicon compound which has heretofore been difficult to obtain industrially can be prepared with ease and in high yield, and the prepared product has a silyl group which is excellent in reactivity, and therefore it has a high utilization value as a functional monomer.

DETAILED DESCRIPTION OF THE INVENTION

Reference will now be made in detail to preferred embodiments of the present invention.

Halogen atoms used in the present invention are preferably F, Cl, Br and I, and above all, Cl and Br are most preferred.

Preferred examples of the halogenated hydrocarbon used in the present invention include $CH_2=CHF$, $CH_2=CHCl$, $CH_2=CHBr$, $CH_2=CHI$, $CH_3-CH=CHCl$, $CH_3CCl=CH_2$, $C_2H_5-CH=CHCl$, $C_3H_7-CH=CHCl$,

$ClHC=CHCl$, $BrCH=CHBr$, $CH_2=CCl_2$, $CCl_2=CCl_2$,

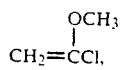

$CH_2=CClCH=CH_2$, $ClHC=CH-CH_2-COOH$, $ClHC=CH-CF_3$, $ClHC=CH-CH_2OH$,

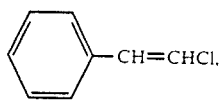

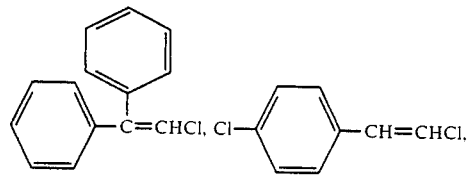

$CH_2=CH-COOCH=CHCl$, $CH_2=C(CH_3)-COOCH=CHCl$, $CH_3OCH=CHCl$, $H_3CHNCH=CHCl$, $(H_3C)_2N-CH=CHCl$, $CH_3CO-CH=CHCl$, $CH_2=CH-CH_2Cl$, $CH_2=CH-CH_2Br$,

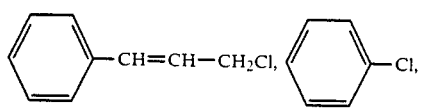

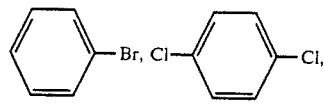

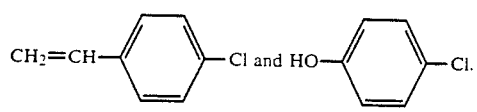

As can be understood from the foregoing list of compounds, the carbon atoms can have substituents such as OH, $NH_2$, COOH and CN. Above, all, the chlorides are used most preferably.

No particularly restriction is imposed on the reaction phase, and so a gaseous phase and a liquid phase are acceptable. In the case that the reaction is performed in the liquid phase, a solvent such as benzene, toluene, xylene, hexane or heptane can be used. With regard to a reaction system, a batch system and a continuous flow system are acceptable. The reaction can be carried out under reduced pressure, atmospheric pressure or increased pressure, but it is preferred that the reaction is performed under increased pressure. Preferably, the pressure is in the range of 1 to 100 $kg/cm^2$. The reaction temperature is in the range of 100° to 650° C., and depends upon the kind of silane and the reactino phase. Preferably, the reaction temperature is from 200° to 650° C. for $SiH_4$, from 100° to 400° C. for $Si_2H_6$, and from 100° to 300° C. for $Si_3H_8$. When the reaction temperature is too high, for example, 650° C. or more, $SiH_4$ is thermally decomposed, so that amorphous silicon deposits occur. When the temperature is 100° C. or less, the reaction rate is low, which is uneconomical.

In the present invention, if the conversion of the silane is increased, the selectivity into the desired product generally tends to decrease. In consequence, a continuous process is desirable in which the conversion of the silane is restricted to a lower level, preferably 10 to 60%, more preferably 20 to 40%, and after the desired product and by-products are removed (distilled), the unreacted silane and halogenated hydrocarbon are recovered and then reused. No particular restriction is imposed on the reactor, but a quenching type reactor is preferable, since such a quenching type reactor can prevent side reactions from occurring.

The reaction proceeds with the aid of heat as described above, but a halogen compound or nitro compound can also be simultaneously used, so that the selectivity into the desired product and yield can be improved. Typical examples of the halogen compound and nitro compound include $CCl_2BrCH_2Br$, $CBrCl_3$, $CCl_4$, $CCl_3COOH$, $CH_3I$,

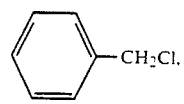

$CBr_4$, $CHI_3$, $CH_2=CH-CH_2Cl$, $CH_2I_2$, $CCl_3CCl_3$, $CHCl_3$, $CH_2Cl_2$, $CCl_3CHCl_2$, $CH_2ClCOOH$, $CH_2BrCH_2Br$, $(CH_3)_2CHCH_2Cl$, $Cl(CH_2)_3Cl$, $CH_3(CH_2)_3Cl$, $CHCl_2CHCl_2$, $(CH_3)_2CHCl$, $CH_3CCl_3$, $CH_2ClCCl_3$, $Br(CH_2)_6Br$, $CHBr_3$, $CH_2Br_2$, $CH_3CH_2Br$, $CHBr_2CHBr_2$, $CH_2BrCHBrCH_2Cl$, $(CH_3)_3CCl$, $CH_3CH_2I$, $CH_2BrCl$, $CH_2ICH_2I$, $CH_2=CHCH_2I$, $(CH_3)_3CBr$,

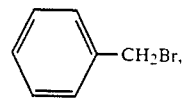

$CHI_3$, $CH_3NO_2$, $CH_3CH_2NO_2$ and $CCl_3NO_2$.

The amount of each of these compounds is in the range of 0.0001 to 0.5 mole, preferably 0.001 to 0.1 mole, more preferably 0.01 to 0.05 mole per mole of the silane. When the amount of the added halogen compound or nitro compound is too small, the effect is insufficient, and when it is too great, the selectivity decreases and the amount of by-products increases.

In the reaction, in addition to the above-mentioned compounds, it is possible to employ the following materials: a halogen such as $Cl_2$ or $ICl$; a catalyst such as activated carbon, $SnCl_4$, $CuCl$, $CoCl_2$, $SnCl_2$, $ZnO$, $AlCl_3$ or $Cu$; a halogenated hydrocarbon-removing agent such as $NH_3$, $(C_2H_5)_3N$, $Na$, $Al$ or $Zn$; a radical initiator such as cumene peroxide, di-t-butyl peroxide, azobisisobutyronitrile or benzoyl peroxide; and $C_6H_4(OH)_2$ or $C_6H_3(OH)_3$.

The compound which can be obtained by the present invention has at least one of a silyl group ($-SiH_3$), disilyl group ($-Si_2H_5$) and trisilyl group ($-Si_3H_7$), and in general, it is represented by the formula:

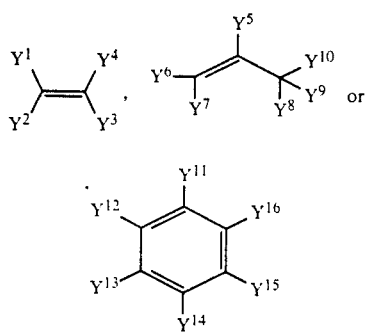

wherein each of $Y^1$ to $Y^{16}$ is selected from the group consisting of hydrogen, an alkyl group, alkenyl group, phenyl group, naphthyl group, alkoxy group, acyl group, alkylamino group and dialkylamino group having 1 to 20 carbon atoms which are unsubstituted or substituted, a halogen atom, silyl group, disilyl group and trisilyl group; and each of at least one of $Y^1$ to $Y^4$, at least one of $Y^8$ to $Y^{10}$ and at least one of $Y^{11}$ to $Y^{16}$ is a silyl group, disilyl group or trisilyl group.

In particular, the compound represented by the formula:

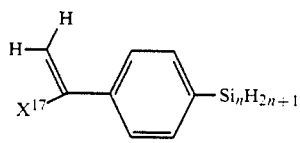

wherein $X^{17}$ is selected from the group consisting of hydrogen, an alkyl group, alkenyl group, phenyl group, naphthyl group, alkoxy group, acyl group, alkylamino group and dialkylamino group having 1 to 20 carbon atoms which are unsubstituted or substituted and a halogen atom, and n denotes 1, 2 or 3, is novel and quite useful. The present invention includes this compound.

The Si-H bond of the silyl group contained in the compound which can be obtained by the present invention is excellent in reactivity, and it can react with various functional groups such as $C\equiv C$, $C=C$, $C=O$,

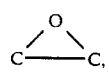

N-H, O-H. Furthermore, in the case that the compound obtained by the present invention is an a-olefin, this compound has a polymerizable double bond (which is suitable for coordinating anion polymerization or radical polymerization) in its molecule and can copolymerize with another olefin. Therefore, when the Si-H bond is introduced into a conventional carbon polymer in accordance with the present invention, a variety of functional polymers can be produced.

Now, the present invention will be hereinafter illustrated by way of the following examples, which are intended to be purely exemplary of the present invention.

The meaning of "Nml" is normal ml, i.e., ml at 0° C., 760 mm Hg.

EXAMPLE 1

$SiH_4$ and $CH_2=CHCl$ were fed at constant flow rates of 25 Nml/minute and 100 Nml/minute, respectively, to a reaction tube having an inner diameter of 16 mm and a height of 100 mm which had been set to 475° C., and reaction was then carried out for 5 hours. The resulting product was collected in a trap cooled to $-100°$ C. or less, and after completion of the reaction, the product was identified and analyzed by means of mass spectroscopy, IR and gas chromatography.

The conversion of the $SiH_4$ was 26%, the main component of the obtained product was vinylsilane in an amount of 3.1 g, and its yield was 16%. The selectivity of the reacted $SiH_4$ into vinylsilane was 62% (this value was based on Si; which shall apply to the following). As by-products, $Si_2H_6$, $H_3SiCl$, $(CH_2=CH)_2SiH_2$, $CH_2CHCHCHSiH_3$, polyvinylsilane, hydrogen chloride and ethylene were obtained.

EXAMPLE 2

The experiment was carried out following the same procedure as in Example 1 except that the $CH_2=CHCl$ was replaced with $CH_2=CHBr$ and the reaction temperature was 425° C.

The conversion of the $SiH_4$ was 22%, the main component of the obtained product was vinylsilane, and its yield was 12%. The selectivity of the reacted $SiH_4$ into vinylsilane was 55%. As by-products, $Si_2H_6$, $H_3SiBr$, $(CH_2=CH)_2SiH_2$, $CH_2CHCHCHSiH_3$, polyvinylsilane, hydrogen bromide and ethylene were obtained.

EXAMPLE 3

The experiment was carried out following the same procedure as in Example 1 except that the $CH_2=CHCl$ was replaced with $CH_2=CH-CH_2Cl$ and the flow rates of $SiH_4$ and $CH_2=CH-CH_2Cl$ were 54 Nml/minute.

The conversion of the $SiH_4$ was 29%, the main component of the obtained product was allylsilane, and its yield was 12%. The selectivity of the reacted $SiH_4$ into allylsilane was 41%. As by-products, $Si_2H_6$, $H_3SiCl$, $(CH_2=CH-CH_2)_2SiH_2$, polyallylsilane, hydrogen chloride and propylene were obtained.

EXAMPLE 4

The experiment was carried out following the same procedure as in Example 1 except that the $CH_2=CHCl$ was replaced with

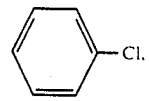

the flow rates of $SiH_4$ and

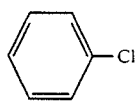

were 58 Nml/minute and 47 Nml/minute, respectively, and the reaction temperature was 500° C.

The conversion of the SiH$_4$ was 20%, the main component of the obtained product was phenylsilane, and its yield was 2%. The selectivity of the reacted SiH$_4$ into phenylsilane was 10%. As by-products, Si$_2$H$_6$, H$_3$SiCl, hydrogen chloride and benzene were obtained.

EXAMPLE 5

The experiment was carried out following the same procedure as in Example 1 except that the CH$_2$=CHCl was replaced with

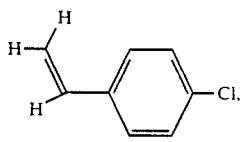

the flow rates of SiH$_4$ and

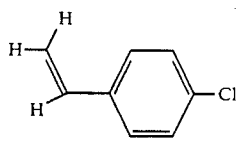

were 50 Nml/minute and 45 Nm/minute, respectively.

The conversion of the SiH$_4$ was 15%, the main component of the obtained product was

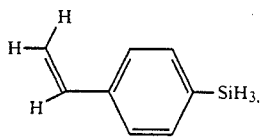

(IR: $\gamma_{Si\text{-}H}$ 2150 cm$^{-1}$, $\delta_{Si\text{-}H}$ 920 cm$^{-1}$, $\gamma_{C\text{-}H}$ 3010 cm$^{-1}$, $\delta_{C=C}$ 1650 cm$^{-1}$, 1490 cm$^{-1}$, $\delta_{C\text{-}C}$ 690 cm$^{-1}$, $\delta_{Si\text{-}C}$ 1120 cm$^{-1}$, $^1$H-NMR: 4.10 ppm (Si-H), 5.05–5.88 ppm (-CH=CH$_2$), 6.45–6.93 ppm (-CH=CH$_2$), 7.22–7.68 ppm

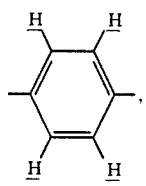

Elementary analysis: C 71.24 (71.57 theoretically) % by weight, H 7.72 (7.51 theoretically) % by weight, Si 20.63 (20.92 theoreticaly) % by weight, Exact MS(EI) m/z=134.0550 (134.0552 theoretically)).

The yield of the product was 1.2% and the selectivity of the reacted SiH$_4$ into the product was 8%. As by-products, Si$_2$H$_6$, H$_3$SiCl, HCl,

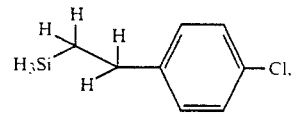

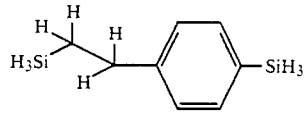

and the like were obtained.

EXAMPLES 6 and 7

The experiments were carried out following the same procedure as in Example 1 except that each of CCl$_4$ (Example 6) and CH$_3$NO$_2$ (Example 7) was fed at a flow rate of 0.7 Nml/minute in addition to SiH$_4$ and CH$_2$=CHCl used as raw materials and the reaction temperatues were 450° C. (Example 6) and 425° C. (Example 7).

In the case that CCl$_4$ was added, the conversion of the SiH$_4$ was 30%, the yield of vinylsilane was 20%. The selectivity into vinylsilane was 68%. On the other hand, in the case that CH$_3$NO$_2$ was added, the conversion was 30%, the yield was 25%, and the selectivity was 64%. By-products were the same as in Example 1.

EXAMPLE 8

The experiment was carried out following the same procedure as in Example 1 except that the SiH$_4$ was replaced with Si$_2$H$_6$ and the reaction temperature was 350° C.

The conversion of the Si$_2$H$_6$ was 21%, the main component of the obtained product was vinyldisilane, and its yield was 3%. The selectivity of the reacted Si$_2$H$_6$ into vinyldisilane was 14%. As by-products, SiH$_4$, H$_3$SiCl, Si$_3$H$_8$, (CH$_2$=CH)$_2$Si$_2$H$_4$, polyvinylsilane, hydrogen chloride and ethylene were obtained.

EXAMPLE 9

In a 70 ml autoclave were placed 48 mmol (5 g) of C$_3$H$_7$-CH=CHCl and about 50 mmol of SiH$_4$, and reaction was then carried out at a reaction temperature of 400° C. for 20 hours. In this case, the reaction pressure was about 41 kg/cm$^2$. After completion of the reaction, the product was identified and analyzed by means of mass spectroscopy, IR and gas chromatography.

The production of C$_3$H$_7$-CH=CH-SiH$_3$ was attained, and its amount was about 0.5 g (the yield of this product with respect to SiH$_4$ was about 10%, but it was based on Si). As by-products, SiH$_2$H$_6$, H$_3$SiCl, (C$_3$H$_7$CH=CH)$_2$SiH$_2$, hydrogen chloride and C$_3$H$_7$-CH=CH$_2$ were obtained.

EXAMPLE 10

The experiment was carried out following the same procedure as in Example 9 except that the C$_3$H$_7$-CH=CHCl was replaced with CHCl=CHCl.

The production of CH$_2$(SiH$_3$)-CH$_2$(SiH$_3$) and CHCl=CH(SiH$_3$) was attained, and the amounts of these products were about 0.9 g (the yield of this product with respect to SiH$_4$ was about 3%, but it was based on Si) and 1.9 g (similarly 6%), respectively.

As by-products, Si$_2$H$_6$, H$_3$SiCl, hydrogen chloride and CH$_2$=CHCl were obtained.

What is claimed is:

1. A process for preparing an organic silicon compound represented by the formula:

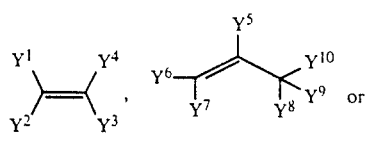, 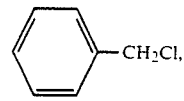 or

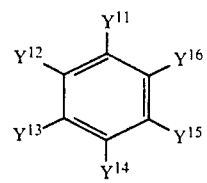

wherein each of $Y^1$ to $Y^{16}$ is selected from the group consisting of hydrogen, an alkyl group, alkenyl group, phenyl group, naphthyl group, alkoxy group, acyl group, alkylamino group and dialkylamino group having 1 to 20 carbon atoms which are unsubstituted or substituted, a halogen atom, silyl group, disilyl group and trisilyl group; and each of at least one of $Y^1$ to $Y^4$, at least one of $Y^8$ to $Y^{10}$ and at least one of $Y^{11}$ to $Y^{16}$ is a silyl group, disilyl group or trisilyl group, which comprises the step of reacting a halogenated hydrocarbon selected from the group consisting of

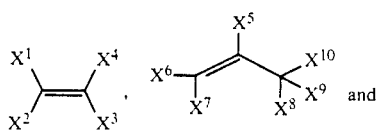, 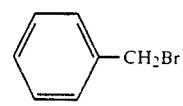 and

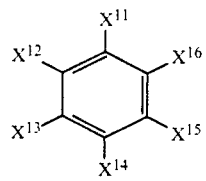

wherein each of $X^1$ to $X^{16}$ is selected from the group consisting of hydrogen, an alkyl group, alkenyl group, phenyl group, naphthyl group, alkoxy group, acyl group, alkylamino group and dialkylamino group having 1 to 20 carbon atoms which are unsubstituted or substituted and a halogen atom; and each of at least one of $X^1$ to $X^4$, at least one of $X^8$ to $X^{10}$ and at least one of $X^{11}$ to $X^{16}$ is a halogen atom, with a silane selected from the group consisting of $SiH_4$, $Si_2H_6$ and $Si_3H_8$.

2. A process for preparing an organic silicon compound according to claim 1 wherein said halogen atom is a chlorine atom.

3. A process for preparing an organic silicon compound according to claim 1 wherein said halogen atom is a bromine atom.

4. A process for preparing an organic silicon compound according to claim 1 wherein said reaction is carried out in the range of 100° to 650° C.

5. A process for preparing an organic silicon compound according to claim 1 wherein said reaction is carried out in the presence of at least one compound selected from the group of halogen compounds consisting of $CCl_2BrCH_2Br$, $CBrCl_3$, $CCl_4$, $CCl_3COOH$, $CH_3I$,

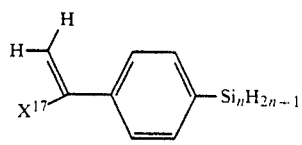

$CBr_4$, $CHI_3$, $CH_2=CH\text{-}CH_2Cl$, $CH_2I_2$, $CH_2BrCH_2Cl$, $CCl_3CCl_3$, $CHCl_3$, $CH_2Cl_2$, $CCl_3CHCl_2$, $CH_2ClCOOH$, $CH_2BrCH_2Br$, $(CH_3)_2CHCH_2Cl$, $Cl(CH_2)_3Cl$, $CH_3(CH_2)_3Cl$, $CHCl_2CHCl_2$, $(CH_3)_2CHCl$, $CH_3CCl_3$, $CH_2ClCCl_3$, $Br(CH_2)_6Br$, $CHBr_3$, $CH_2Br_2$, $CH_3CH_2Br$, $CHBr_2CHBr_2$, $CH_2BrCHBrCH_2Cl$, $(CH_3)_3CCl$, $CH_3CH_2I$, $CH_2BrCl$, $CH_2ICH_2I$, $CH_2=CHCH_2I$, $(CH_3)_3CBr$, and $CHI_3$, and the group of nitro compounds consisting of $CH_3NO_2$, $CH_3CH_2NO_2$ and $CCl_3NO_2$.

6. A process for preparing an organic silicon compound according to claim 5 wherein the total amount of the compounds selected from the groups of said halogen compounds and nitro compounds is from 0.001 to 0.5 mole per mole of said silane.

7. A process for preparing an organic silicon compound according to claim 1 wherein in said reaction, the conversion of said silane is in the range of 10 to 60%.

8. A process for preparing an organic silicon compound according to claim 1 wherein in said reaction, the conversion of said silane is in the range of 10 to 60%, and the unreacted silane and halogenated hydrocarbon are separated and recovered.

9. An organic silicon compound represented by the formula.

wherein $X^{17}$ is selected from the group consisting of hydrogen, an alkyl group, alkenyl group, phenyl group, naphthyl group, alkoxy group, acyl group, alkylamino group and dialkylamino group having 1 to 20 carbon atoms which are unsubstituted or substituted and a halogen atom, and n denotes 1, 2 or 3.

* * * * *